United States Patent
Otsuka

(10) Patent No.: US 7,152,493 B2
(45) Date of Patent: Dec. 26, 2006

(54) SPECIMEN CREATING DEVICE

(75) Inventor: Yuzo Otsuka, Tokyo (JP)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 10/529,383

(22) PCT Filed: Oct. 9, 2003

(86) PCT No.: PCT/JP03/12960

§ 371 (c)(1),
(2), (4) Date: Mar. 28, 2005

(87) PCT Pub. No.: WO2004/038383

PCT Pub. Date: May 6, 2004

(65) Prior Publication Data
US 2006/0042408 A1   Mar. 2, 2006

(30) Foreign Application Priority Data
Oct. 22, 2002   (JP) .............................. 2002-307050

(51) Int. Cl.
 *G01N 1/08* (2006.01)
 *G01N 1/34* (2006.01)
 *B65B 61/00* (2006.01)
(52) U.S. Cl. ..................... 73/864.41; 83/919
(58) Field of Classification Search ............. 73/864.41, 73/865.8, 866, 866.4; 83/919
See application file for complete search history.

(56) References Cited

U.S. PATENT DOCUMENTS 4,382,513 A * 5/1983 Schirmer et al. ........... 206/484
4,447,494 A * 5/1984 Wagner et al. .............. 428/349
4,934,199 A * 6/1990 Avila et al. .......... 73/864.41 X
4,984,409 A * 1/1991 Focke ............................ 53/53
5,341,696 A * 8/1994 Benedikt et al. .............. 73/827

(Continued)

FOREIGN PATENT DOCUMENTS

DE         3920484 A1 *   1/1991

(Continued)

OTHER PUBLICATIONS

Scherz, Jean-Claude; Tetra Brik Packaging Systems Test Methods, Oct. 17, 1995, 19 pages Materials R & D—site Romont (CH).

*Primary Examiner*—Thomas P. Noland
(74) *Attorney, Agent, or Firm*—Bacon & Thomas, PLLC

(57) ABSTRACT

An object is to provide an inspection sample making apparatus (30) that can simplify work for making an inspection sample (12) and can ensure inspection for seal condition. The inspection sample making apparatus (30) includes a preliminary-inspection-sample-making device (20) for peeling a predetermined fusion-bonded piece of a packaging container (10) off a wall of the packaging container (10) so as to make a preliminary inspection sample (20); and a cutting device for cutting the preliminary inspection sample (52) along a predetermined cutting line so as to make an inspection sample (12). Since the preliminary-inspection-sample-making device (20) peels a predetermined fusion-bonded piece of the packaging container (10) off a wall of the packaging container (10) to thereby make the preliminary inspection sample (52), and the cutting device cuts the preliminary inspection sample (52) along a predetermined cutting line to thereby make the inspection sample (12), an operator does not need to manually make the inspection sample (12). Therefore, not only is work for making the inspection sample (12) simplified, but also cutting at a wrong position is avoided. As a result, a seal condition inspection apparatus (31) can reliably inspect seal condition.

15 Claims, 13 Drawing Sheets

U.S. PATENT DOCUMENTS

| | | | |
|---|---|---|---|
| 5,383,322 A * | 1/1995 | Collins et al. | 53/53 |
| 5,526,705 A * | 6/1996 | Skotnikov et al. | 73/863 |
| 5,582,344 A * | 12/1996 | Lawson et al. | 229/217 |
| 5,675,096 A * | 10/1997 | Hydeman et al. | 73/864.41 |
| 5,738,268 A * | 4/1998 | VanderPol et al. | 83/919 X |
| 7,015,700 B1 * | 3/2006 | Konno et al. | 324/444 |
| 7,036,287 B1 * | 5/2006 | Webb | 53/53 |
| 2003/0234239 A1 * | 12/2003 | Lee et al. | 219/109 |
| 2005/0283332 A1 * | 12/2005 | Webb | 702/108 |
| 2006/0109013 A1 * | 5/2006 | Kinoshita et al. | 324/718 |
| 2006/0175560 A1 * | 8/2006 | Yokote | 250/559.45 |

FOREIGN PATENT DOCUMENTS

WO    WO 97/07025    *    2/1997

* cited by examiner

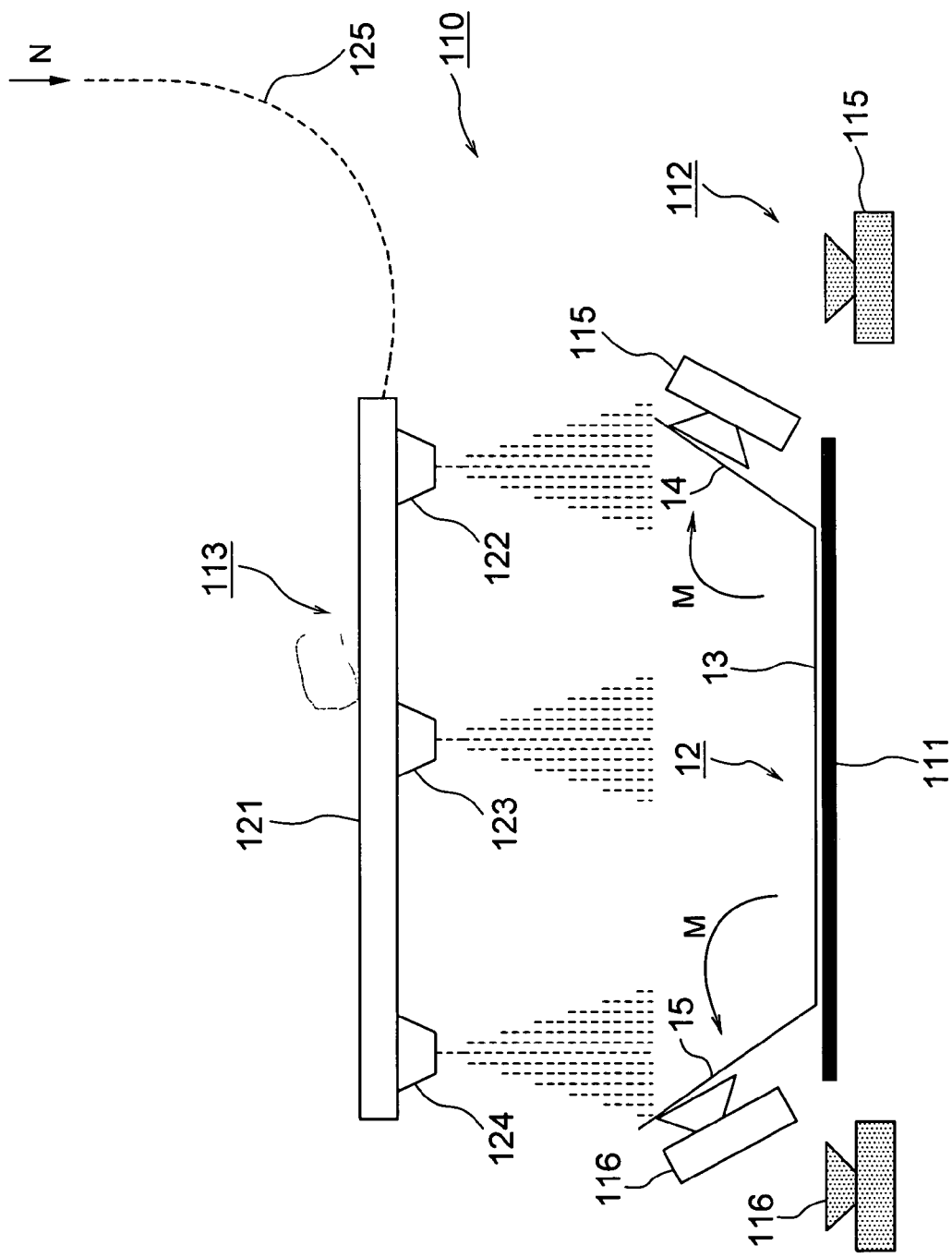

SPECIMEN CREATING DEVICE

CROSS-REFERENCE TO RELATED APPLICATIONS

This application is a National Phase Application (35 USC 371) of PCT/JP2003/012960 and claims priority of Japanese Application No. 2002-307050 filed Oct. 22, 2002.

TECHNICAL FIELD

The present invention relates to an inspection sample making apparatus.

BACKGROUND ART

Conventionally, in production of packaging containers that contain liquid food such as milk or soft drink, a web-like packaging material, a sheet-like packaging material, or the like is formed into packaging containers by means of sealing at predetermined positions through heat sealing, ultrasonic sealing, or a like method. For example, in the case of using a web-like packaging material, the web-like packaging material is formed into a tubular shape; the tubular packaging material is sealed in the longitudinal direction by means of a longitudinal sealing device, which serves as a first sealing device; while being filled with liquid food, the longitudinally sealed tubular packaging material is sealed in the lateral direction and cut at predetermined intervals by means of a lateral sealing device, which serves as a second sealing device, to thereby yield a pillow-like prototype container; and the prototype container is formed into a final packaging container.

Meanwhile, in order to seal the above-mentioned packaging material, the packaging material is gripped from opposite sides with a predetermined gripping force, and resin on the surfaces of the packaging material is melted through application of heat, thereby fusing together the surfaces of the packaging material. However, for example, under a certain condition, such as a certain gripping force, a certain sealing temperature, or a certain resin property, molten resin escapes from a seal portion. As a result, the amount of resin remaining in the seal portion becomes insufficient, potentially resulting in occurrence of a seal defect. Occurrence of a seal defect involves leakage of liquid food from a packaging container or entry of air into the packaging container, with a resultant deterioration in the quality of liquid food.

Thus, in accordance with an inspection manual, an operator inspects a seal portion for seal condition. Specifically, the operator samples completed packaging containers in accordance with the manual; empties the sampled packaging containers of liquid food; cuts the empty packaging containers open by use of a cutter or the like; cleans and dries the opened packaging containers to thereby make inspection samples; and visually inspects seal portions for seal condition from the inside of each of the inspection samples.

However, the above-mentioned conventional method for making an inspection sample requires an operator to manually make an inspection sample, thus involving troublesome work. Also, if the operator cuts the sampled packaging container at a wrong position, inspection for seal condition will become unreliable.

An object of the present invention is to solve the above-mentioned problem in the conventional method for making an inspection sample and to provide an inspection sample making apparatus that can simplify work for making an inspection sample and can ensure inspection for seal condition.

DISCLOSURE OF THE INVENTION

To achieve the above object, an inspection sample making apparatus of the present invention comprises a preliminary-inspection-sample-making device for peeling a predetermined fusion-bonded piece of a packaging container off a wall of the packaging container so as to make a preliminary inspection sample; and a cutting device for cutting the preliminary inspection sample along a predetermined cutting line so as to make an inspection sample.

In this case, the preliminary-inspection-sample-making device peels a predetermined fusion-bonded piece of a packaging container off a wall of the packaging container, thereby making a preliminary inspection sample. The cutting device cuts the preliminary inspection sample along a predetermined cutting line, thereby making an inspection sample. Thus, an operator does not need to manually make an inspection sample. Therefore, not only is work for making an inspection sample simplified, but also cutting at a wrong position is avoided. As a result, a seal condition inspection apparatus can reliably inspect seal condition.

In another inspection sample making apparatus of the present invention, the preliminary-inspection-sample-making device comprises a drive section and a peeling piece, which is rotated through activation of the drive section.

The peeling piece comprises an insert portion to be inserted between the fusion-bonded piece and the wall.

In still another inspection sample making apparatus of the present invention, the peeling piece is formed of a thin plate.

In yet another inspection sample making apparatus of the present invention, the cutting device comprises a first cutting device for cutting the preliminary inspection sample along a laterally predetermined first cutting line, and a second cutting device for cutting the preliminary inspection sample along longitudinally predetermined second and third cutting lines.

In a further inspection sample making apparatus of the present invention, the first cutting device comprises a cutting tool.

In a still further inspection sample making apparatus of the present invention, the second cutting device comprises first and second blades.

A still further inspection sample making apparatus of the present invention further comprises a cleaning device for cleaning the preliminary inspection sample.

In a still further inspection sample making apparatus of the present invention, the cleaning device comprises a press member for ejecting a liquid food from the inside of the preliminary inspection sample.

A still further inspection sample making apparatus of the present invention further comprises a drying device for drying the inspection sample.

A still further inspection sample making apparatus of the present invention further comprises an opening mechanism for opening the inspection sample. The drying device dries the inspection sample in an opened condition.

In a still further inspection sample making apparatus of the present invention, the inspection sample comprises at least two plate-like portions which are fusion-bonded together at a fusion bond portion.

BRIEF DESCRIPTION OF DRAWINGS

FIG. 16 is a front view showing a drying step according to the embodiment of the present invention.

BEST MODE FOR CARRYING OUT THE INVENTION

An embodiment of the present invention will next be described in detail with reference to the drawings.

Figure 1:
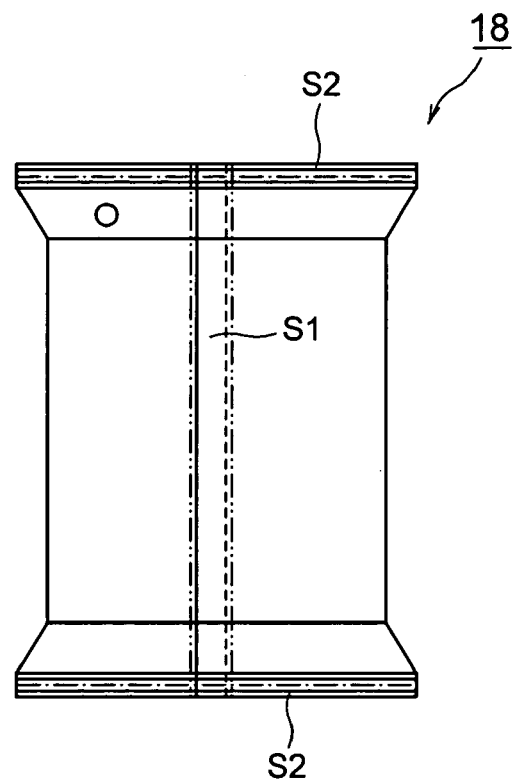
FIG. 1 is a front view of a prototype container associated with an embodiment of the present invention.
Figure 2:
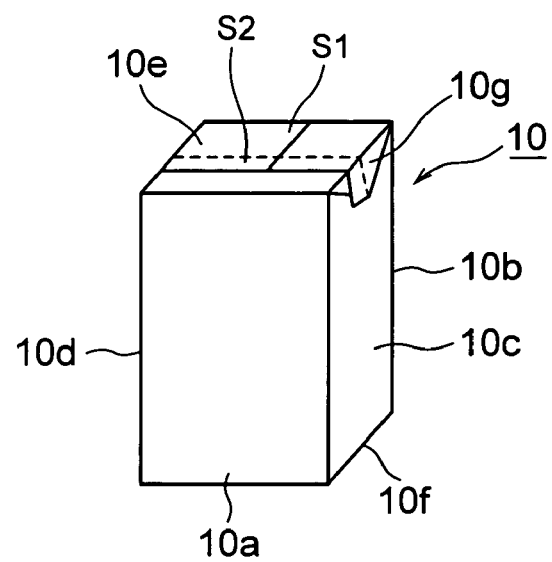
FIG. 2 is a perspective view of a packaging container associated with the embodiment of the present invention.

FIG. 1 is a front view of a prototype container associated with the embodiment of the present invention, and FIG. 2 is a perspective view of a packaging container associated with the embodiment of the present invention.

In FIGS. 1 and 2, reference numeral 10 denotes a packaging container, and reference numeral 18 denotes a prototype container. The packaging container 10 includes a front wall 10a; a back wall 10b; side walls 10c and 10d; a top wall 10e; a bottom wall 10f; a pair of top flaps 10g (FIG. 2 shows only a single top flap 10g), the pair being bent onto the side walls 10c and 10d from the top wall 10e and serving as a first fusion-bonded piece or a first lug; and an unillustrated pair of bottom flaps, the pair being bent from the side walls 10c and 10d onto the bottom wall 10f and serving as a second fusion-bonded piece or a second lug. The top flaps 10g are fusion-bonded to the corresponding side walls 10c and 10d by melting resin. Similarly, the bottom flaps are fusion-bonded to the bottom wall 10f by melting resin.

In this case, a longitudinal seal portion S1 is formed in such a manner as to extend on the top wall 10e, the back wall 10b, and the bottom wall 10f. A lateral seal portion S2 associated with the top wall 10e is formed in such a manner as to extend on the top wall 10e and the top flaps 10g, and a lateral seal portion S2 associated with the bottom wall 10f is formed in such a manner as to extend on the bottom wall 10f and the bottom flaps.

The packaging container 10 is formed, for example, through a filling apparatus working on a web-like packaging material.

Specifically, a web-like packaging material is set on a delivery unit of the filling apparatus; is delivered by means of the delivery unit; and is caused to travel through the filling apparatus by means of a feed unit. While the packaging material is traveling, a hole is punched in the packaging material, and an inner tape and a pull tab are affixed to the packaging material in such a manner as to cover the punched hole. Subsequently, the packaging material is caused to travel vertically. While being guided by a plurality of forming rings disposed along the traveling direction, the vertically traveling packaging material is formed into a tubular shape. The tubular packaging material is sealed in the longitudinal direction by means of a longitudinal sealing device. In this manner, the longitudinal seal portion S1 is formed.

Subsequently, liquid food is supplied from above into the packaging-material tube via a filling pipe. Next, a lateral sealing device grips the packaging-material tube from opposite sides, and the packaging-material tube is laterally sealed at predetermined longitudinal intervals, thereby forming lateral seal portions S2. The packaging-material tube is cut at the lateral seal portions S2 and is formed into the pillow-like prototype container 18 through deformation effected by forming flaps.

Meanwhile, in order to seal the above-mentioned packaging material, the packaging material is gripped from opposite sides with a predetermined gripping force, and resin on the surfaces of the packaging material is melted through application of heat, thereby fusing together the surfaces of the packaging material. However, for example, under a certain condition, such as a certain gripping force, a certain sealing temperature, or a certain resin property, molten resin escapes from a seal portion, such as the longitudinal seal portion S1 or the lateral seal portion S2. As a result, the amount of resin remaining in the seal portion becomes insufficient, potentially resulting in occurrence of a seal defect. Occurrence of a seal defect involves leakage of liquid food from the packaging container 10 or entry of air into the packaging container 10, with a resultant deterioration in the quality of liquid food.

Thus, the completed packaging containers 10 undergo predetermined sampling. The sampled packaging containers 10 are cut open to thereby become inspection samples. The inspection samples are inspected for seal condition at seal portions.

Next, an apparatus and a method for making an inspection sample will be described.

Figure 3:
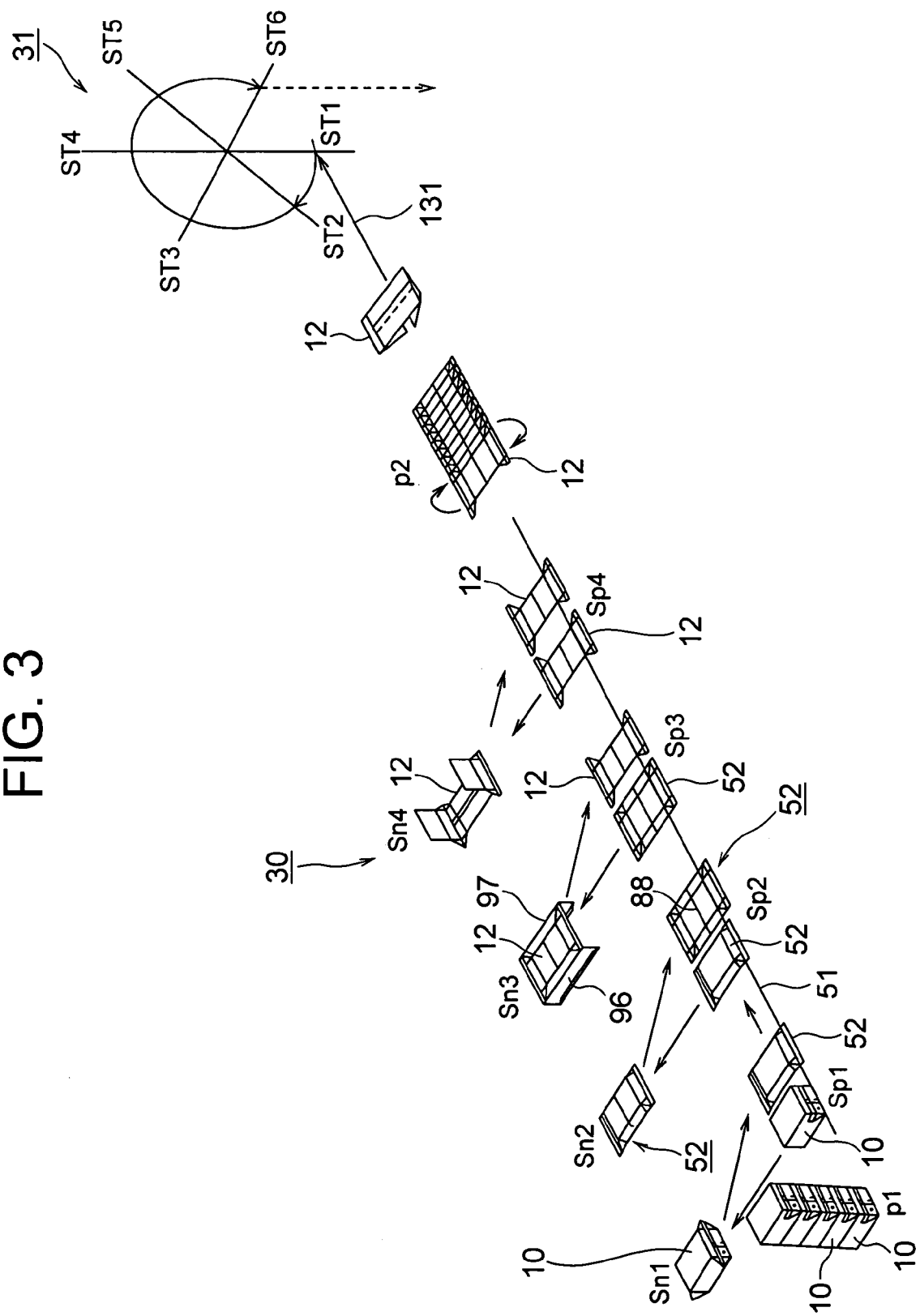
FIG. 3 is a perspective view showing a method for making an inspection sample according to the embodiment of the present invention.
Figure 4:
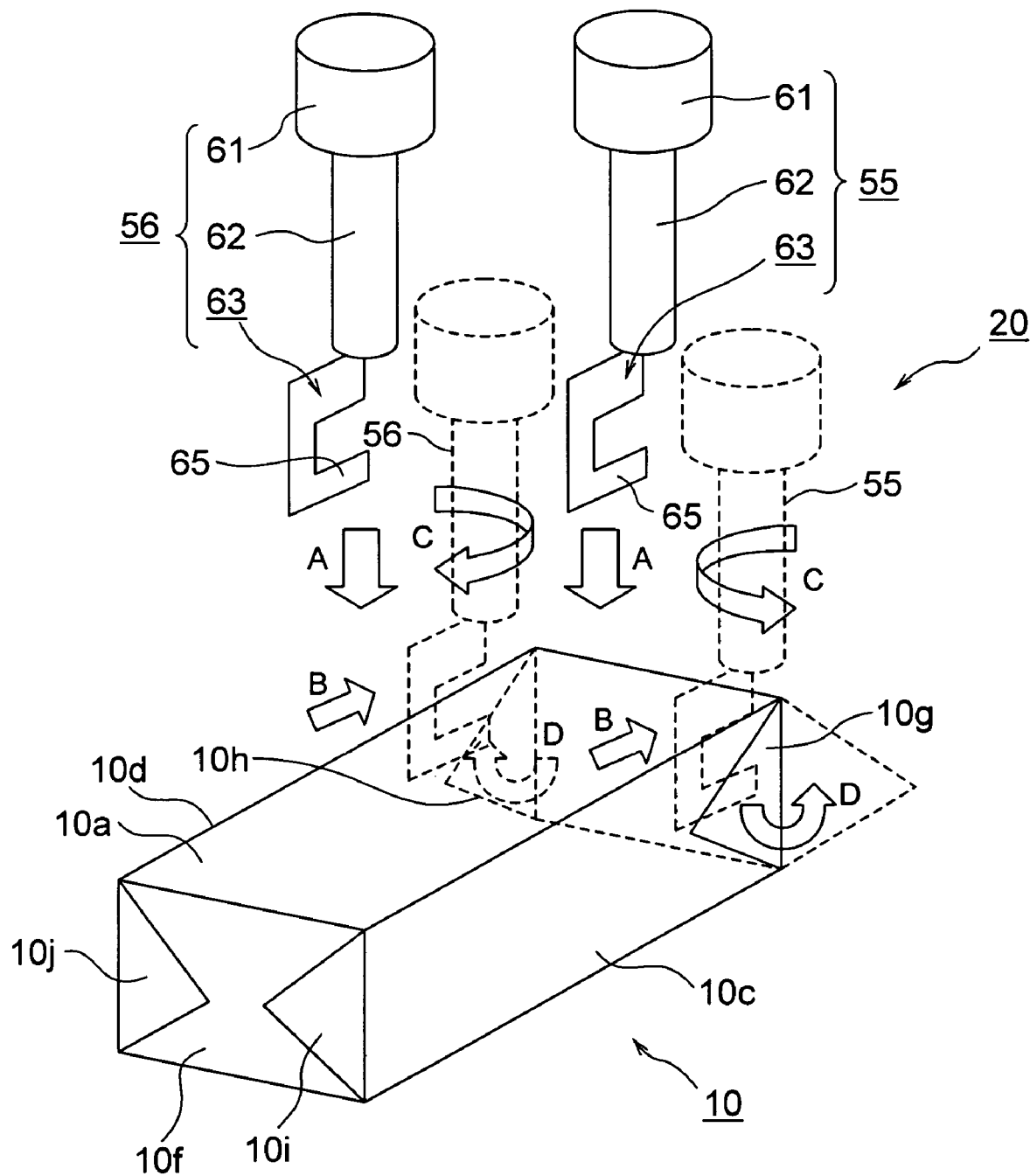
FIG. 4 is a first perspective view showing a preliminary-inspection-sample-making step according to the embodiment of the present invention.
Figure 5:
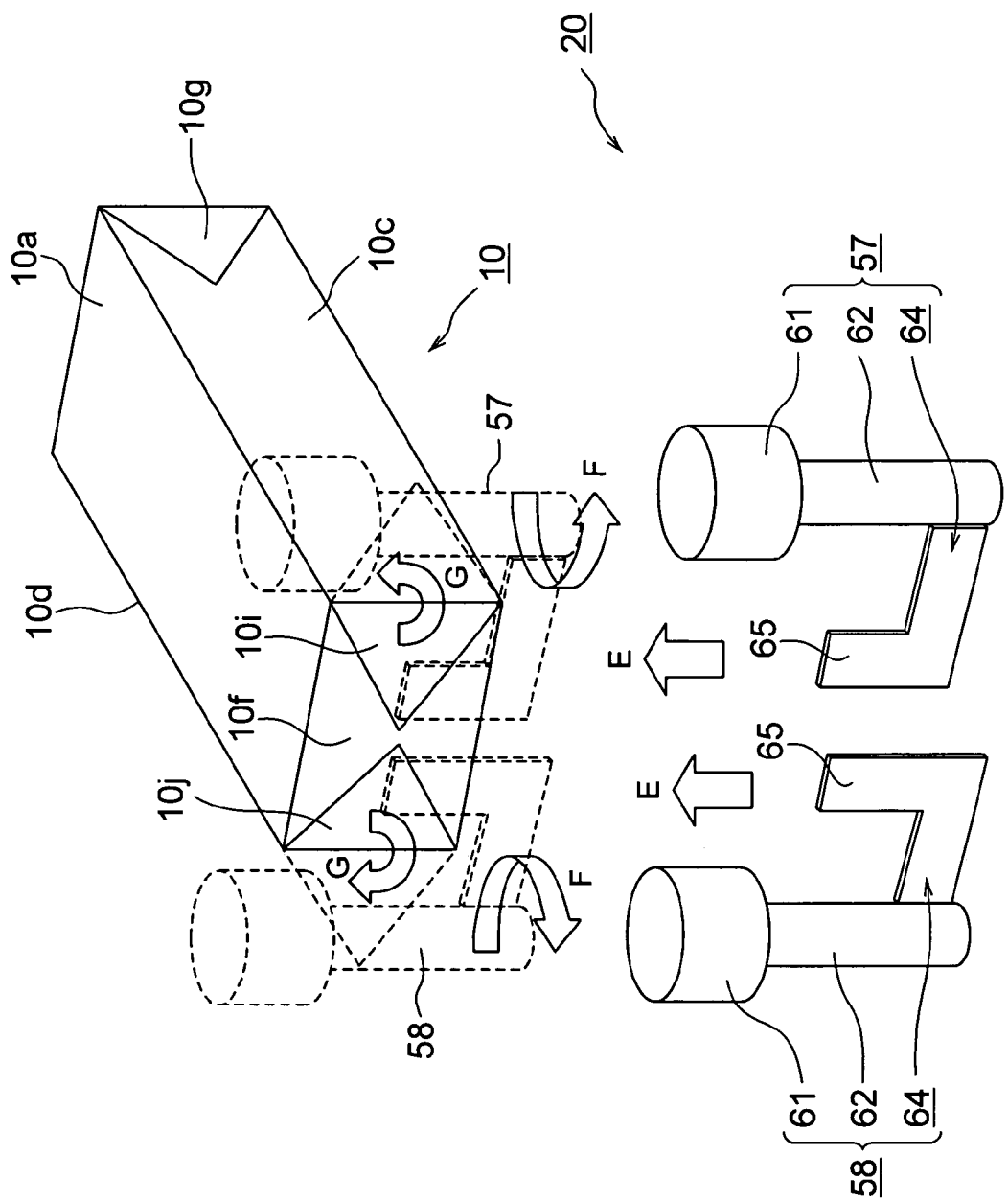
FIG. 5 is a second perspective view showing the preliminary-inspection-sample-making step according to the embodiment of the present invention.
Figure 6:
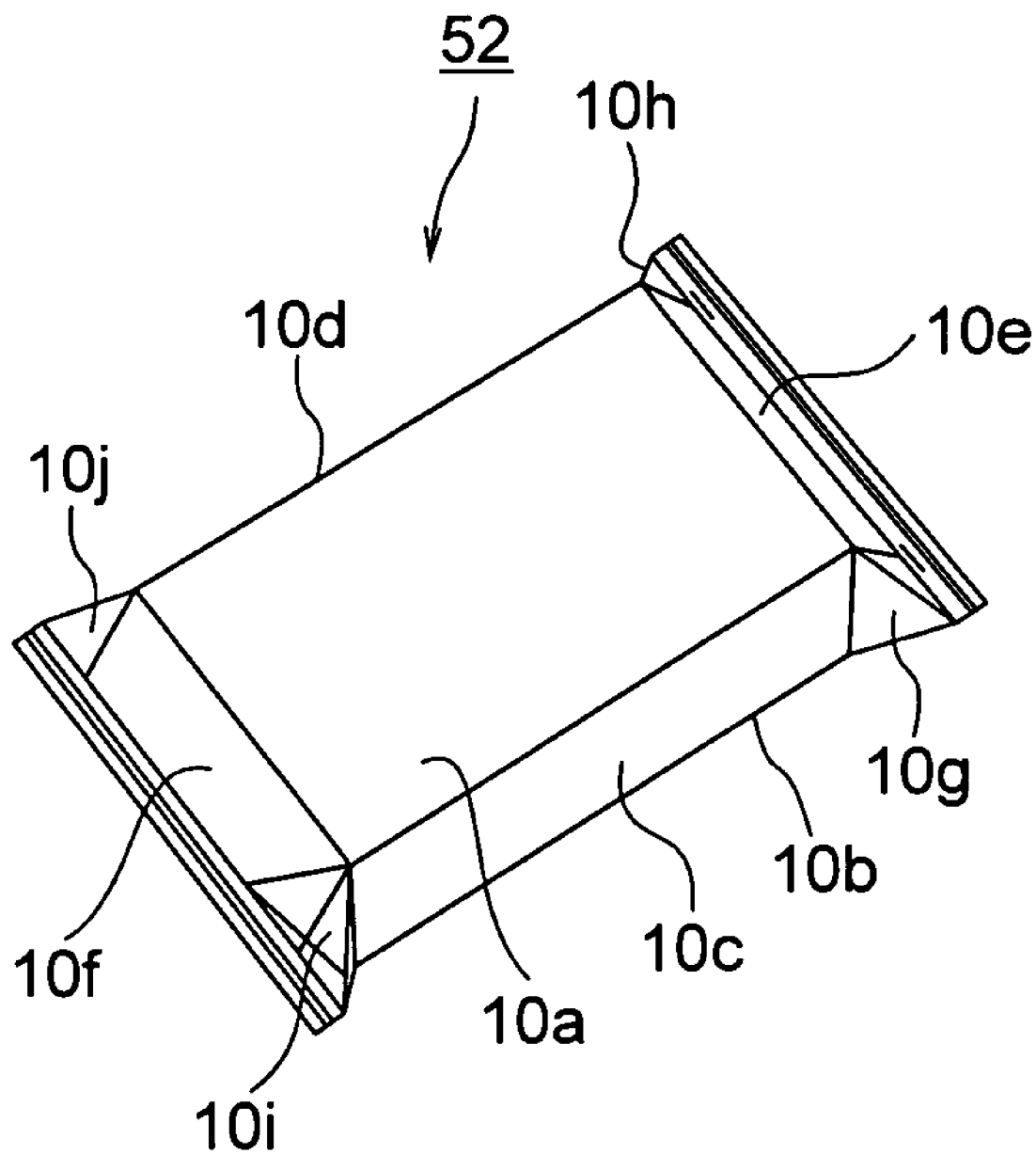
FIG. 6 is a perspective view of a preliminary inspection sample associated with the embodiment of the present invention.
Figure 7:
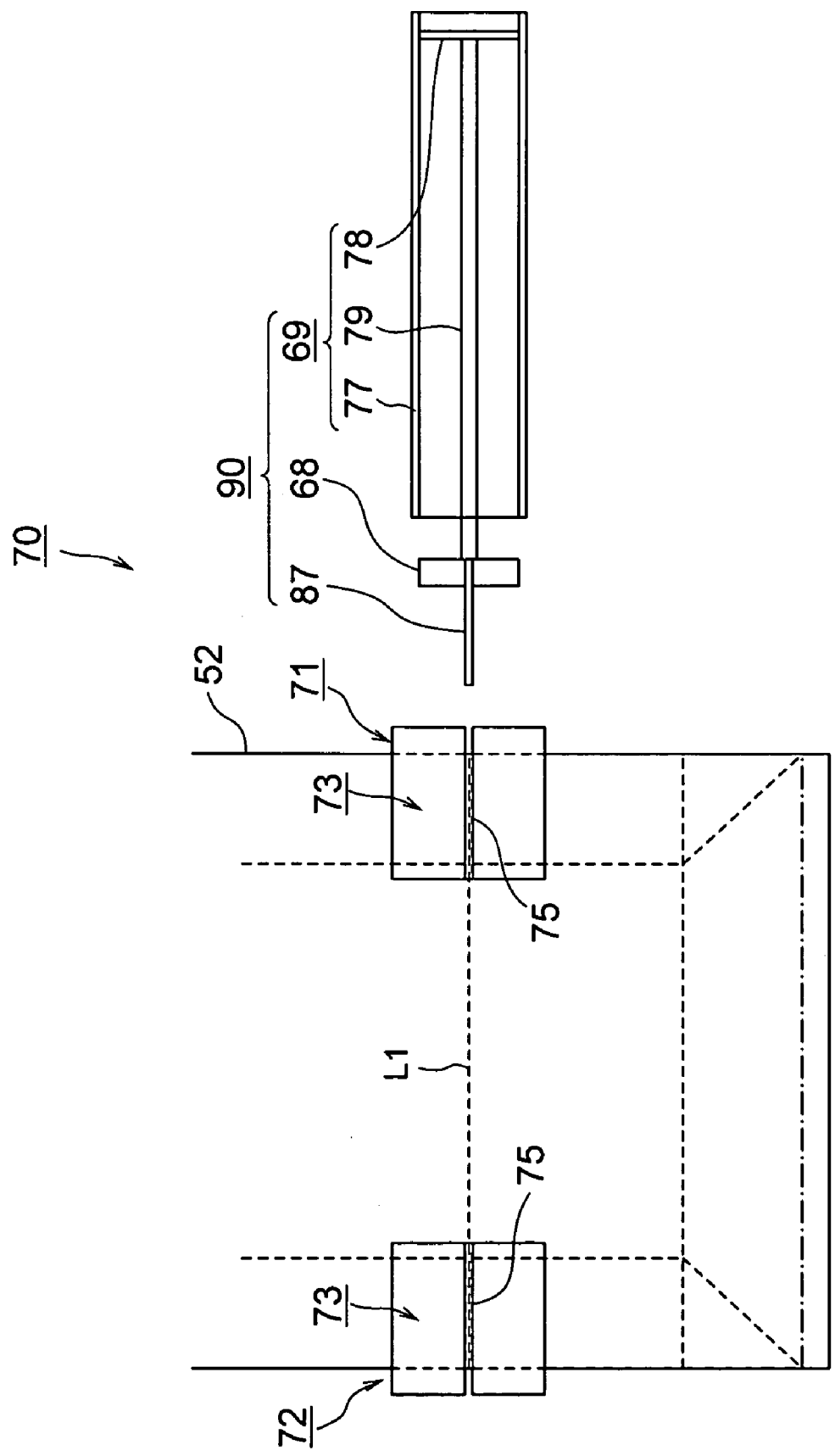
FIG. 7 is a plan view showing a first cutting step according to the embodiment of the present invention.
Figure 8:
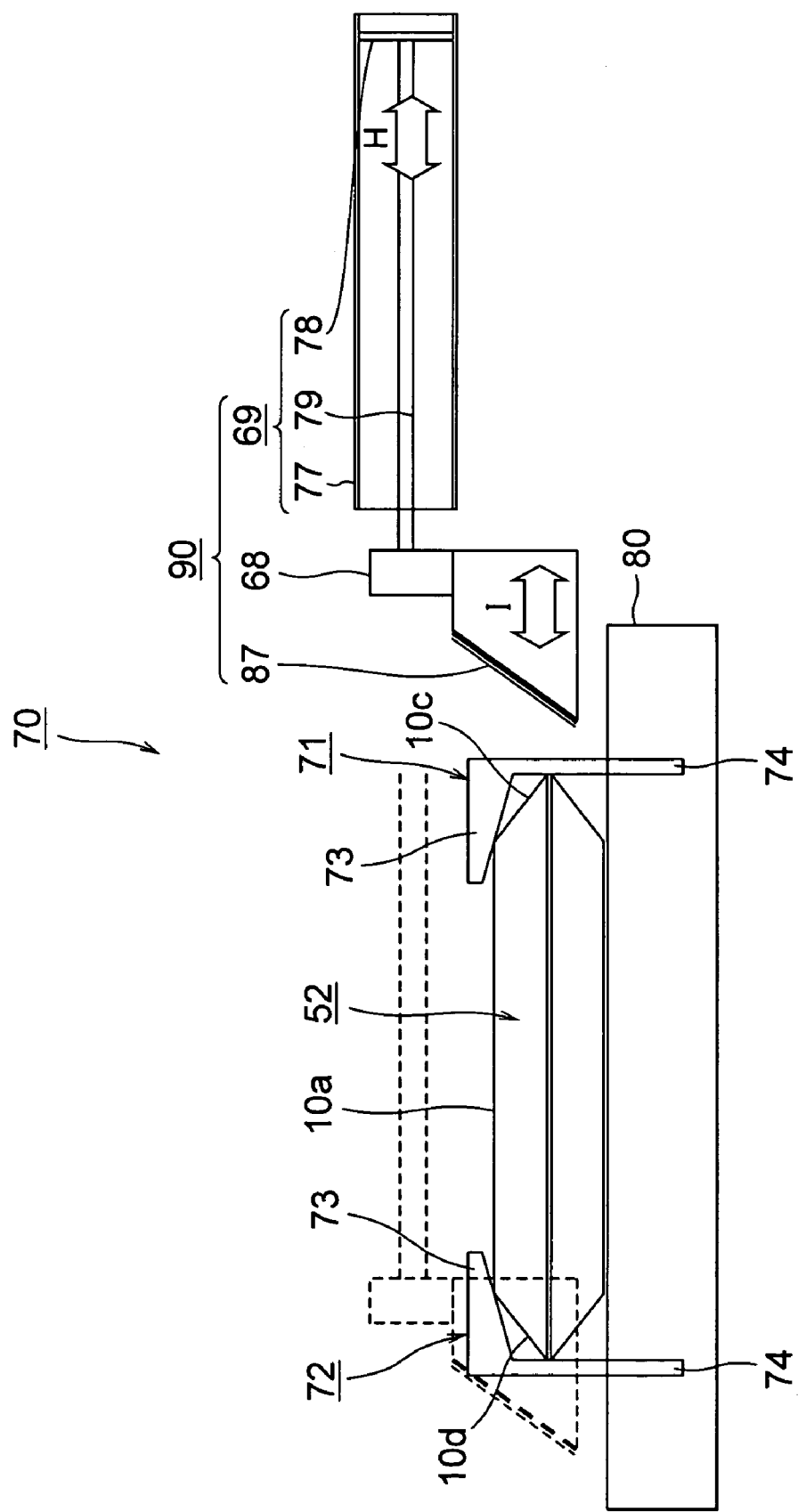
FIG. 8 is a front view showing the first cutting step according to the embodiment of the present invention.
Figure 9:
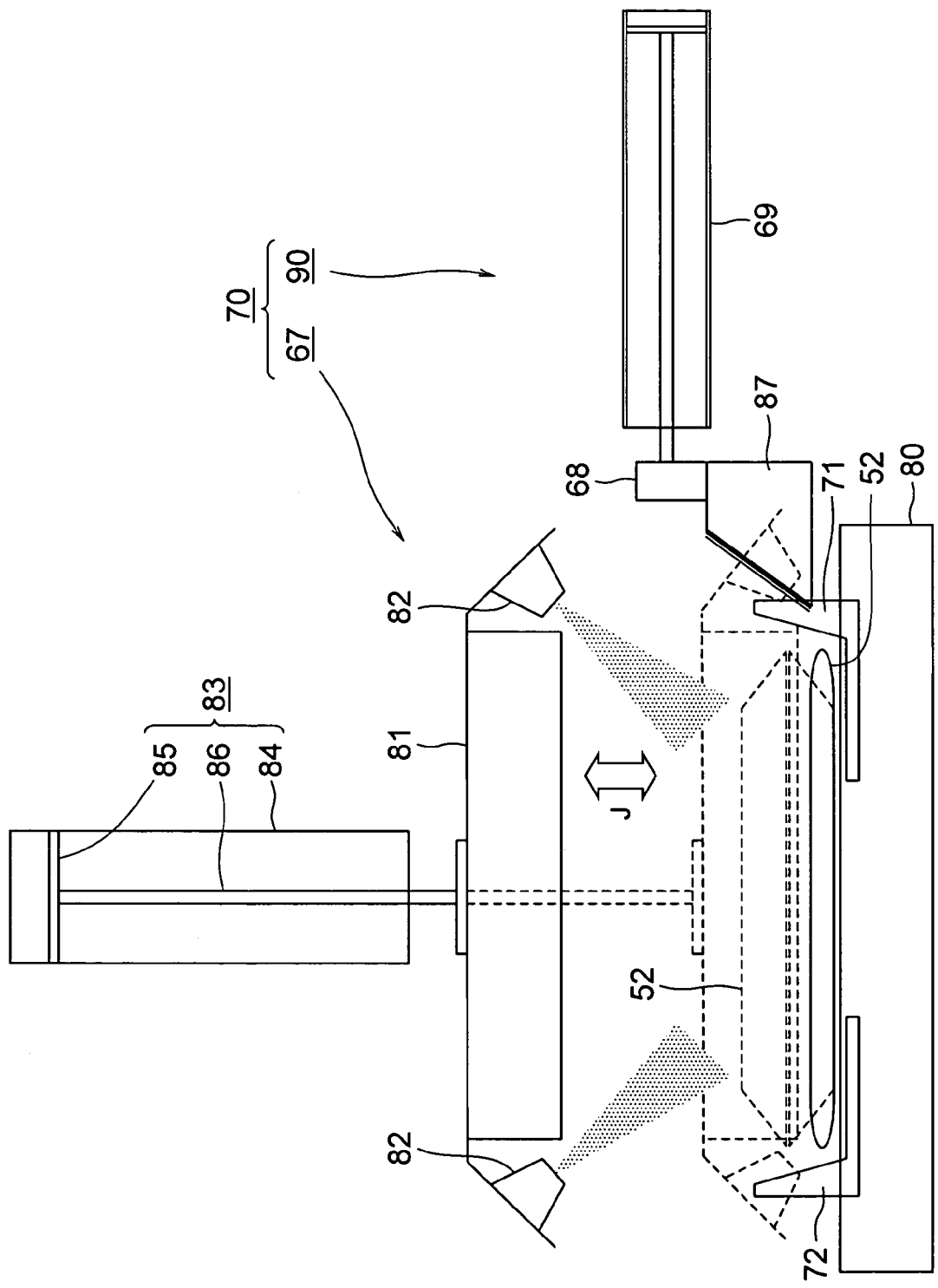
FIG. 9 is a front view showing a cleaning step according to the embodiment of the present invention.
Figure 10:
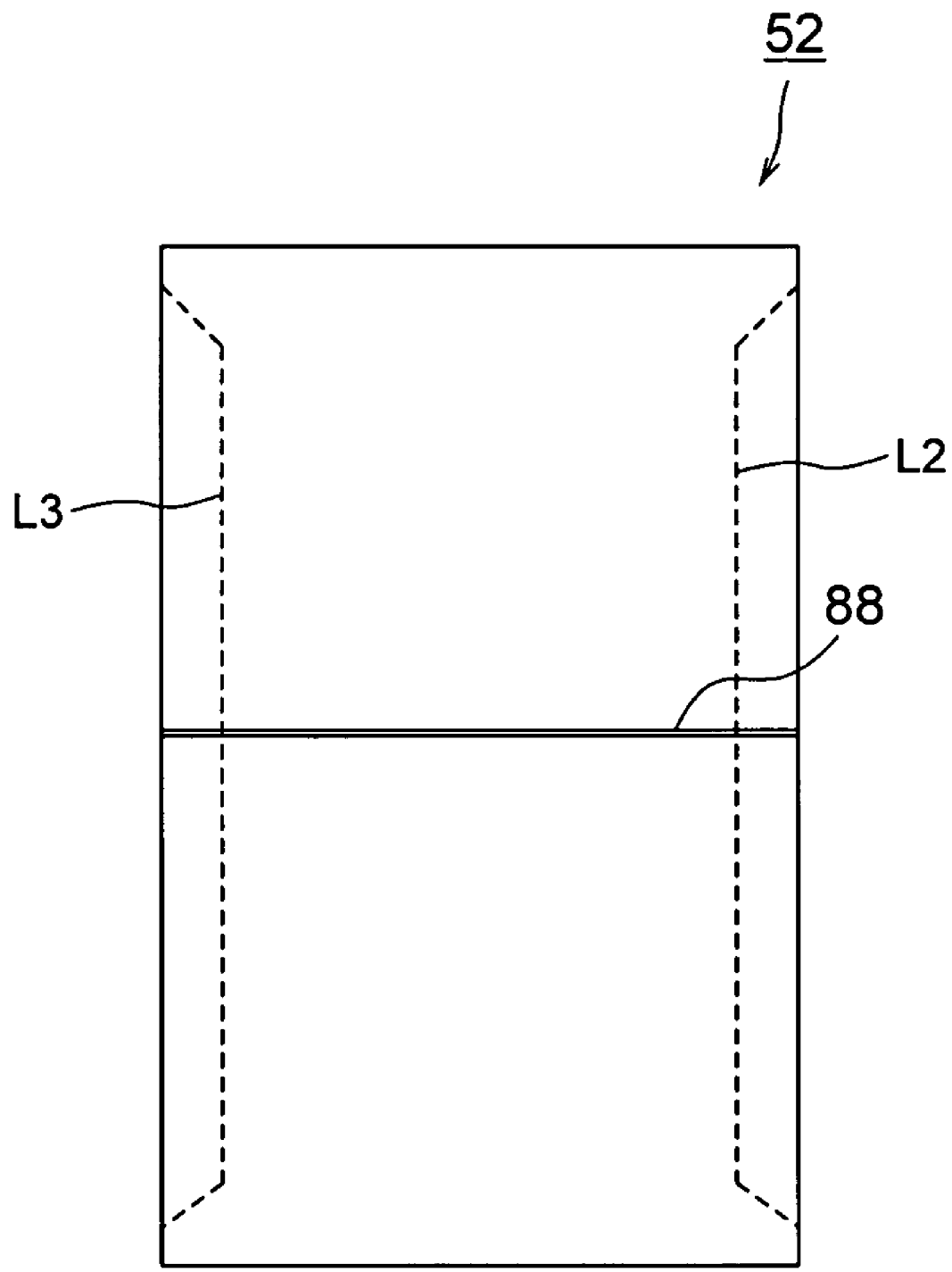
FIG. 10 is a plan view showing the preliminary inspection sample associated with the embodiment of the present invention as viewed after the first cutting step and the cleaning step.
Figure 11:
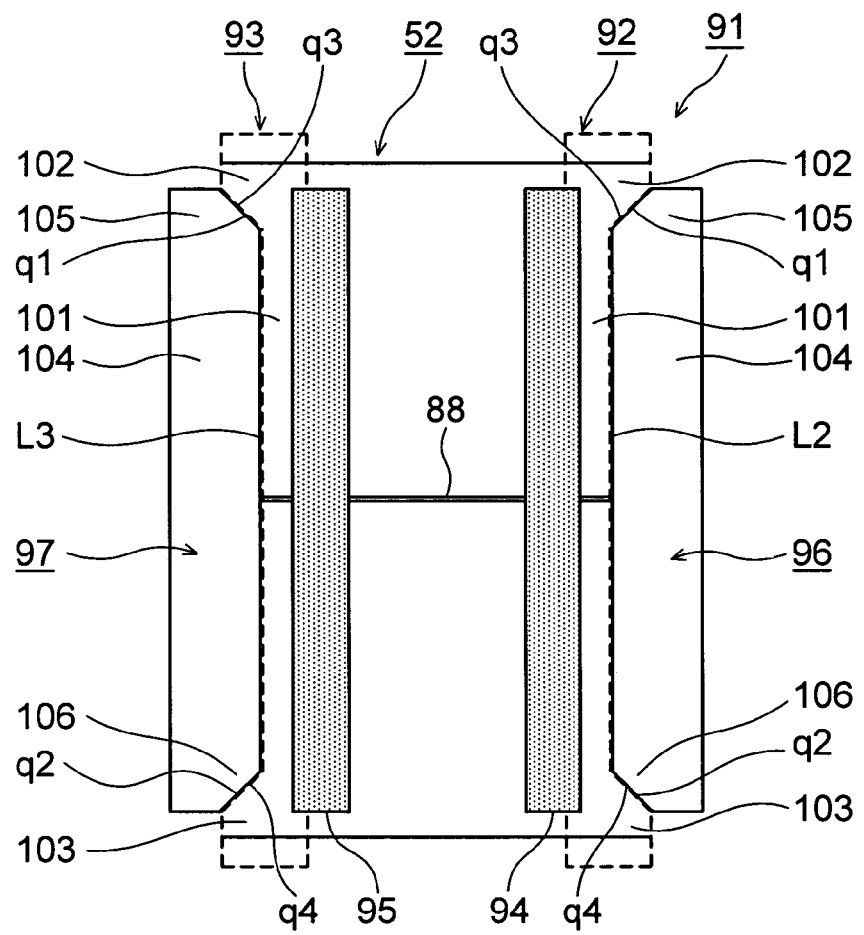
FIG. 11 is a plan view showing the relationship between the preliminary inspection sample and a cutting device according to the embodiment of the present invention.
Figure 12:
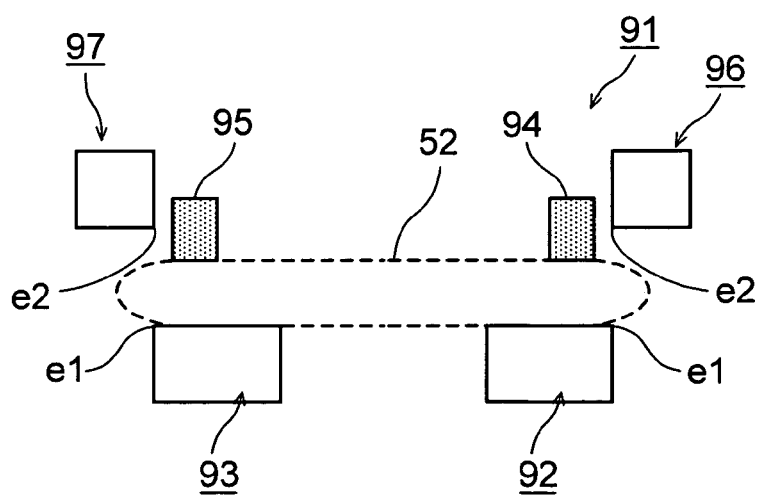
FIG. 12 is a front view showing the relationship between the preliminary inspection sample and the cutting device according to the embodiment of the present invention.
Figure 13:
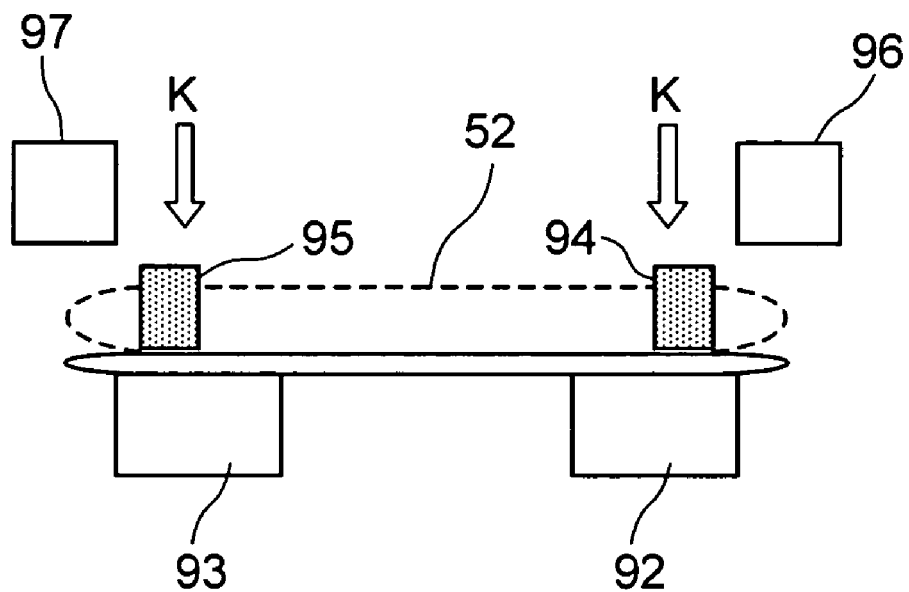
FIG. 13 is a first front view showing a second cutting step according to the embodiment of the present invention.
Figure 14:
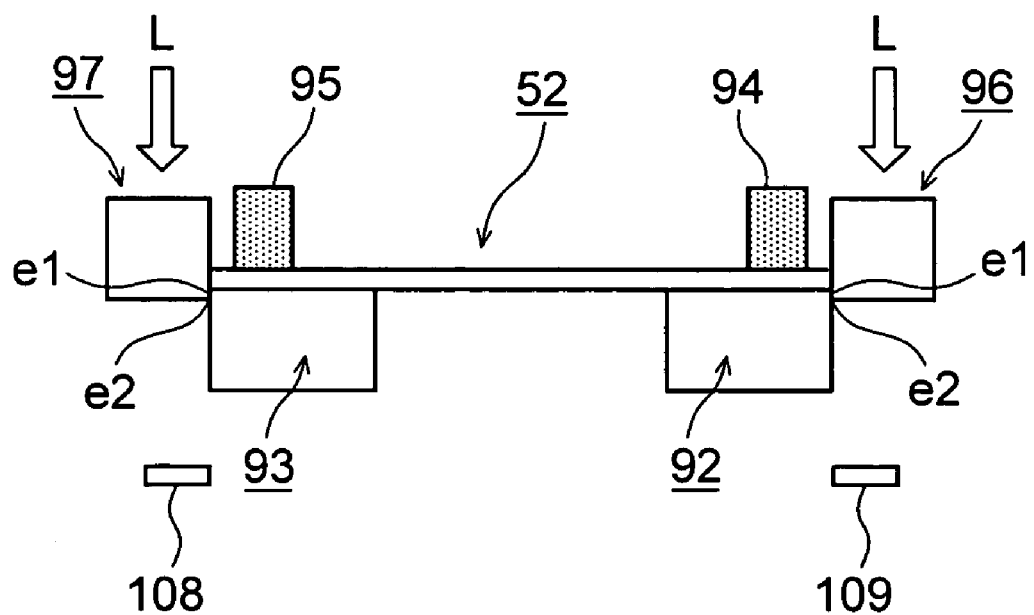
FIG. 14 is a second front view showing the second cutting step according to the embodiment of the present invention.
Figure 15:
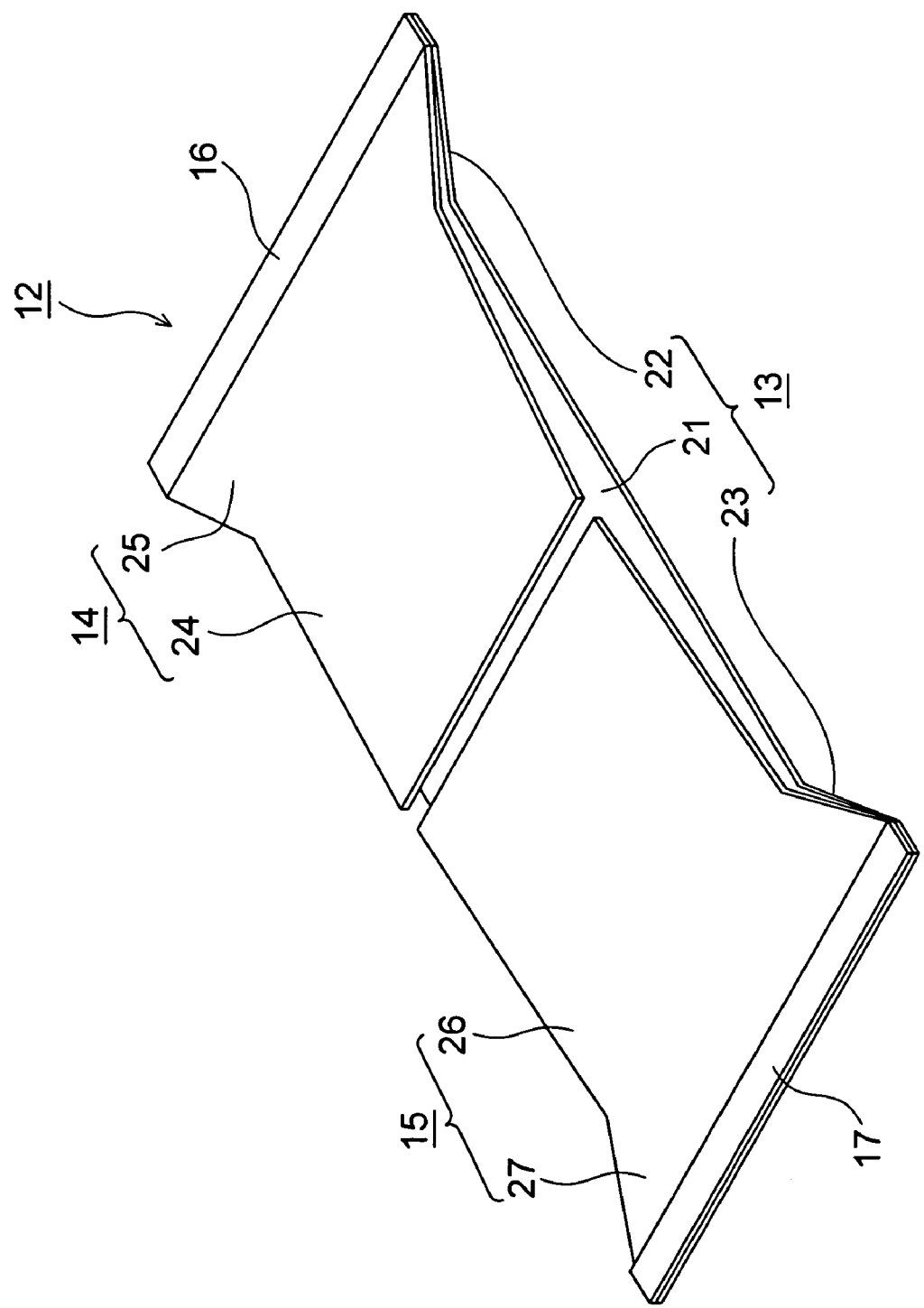
FIG. 15 is a perspective view showing an inspection sample associated with the embodiment of the present invention.

FIG. 3 is a perspective view showing a method for making an inspection sample according to the embodiment of the present invention; FIG. 4 is a first perspective view showing a preliminary-inspection-sample-making step according to the embodiment of the present invention; FIG. 5 is a second perspective view showing the preliminary-inspection-sample-making step according to the embodiment of the present invention; FIG. 6 is a perspective view of a preliminary inspection sample associated with the embodiment of the present invention; FIG. 7 is a plan view showing a first cutting step according to the embodiment of the present invention; FIG. 8 is a front view showing the first cutting step according to the embodiment of the present invention; FIG. 9 is a front view showing a cleaning step according to the embodiment of the present invention; FIG. 10 is a plan view showing the preliminary inspection sample associated with the embodiment of the present invention as viewed after the first cutting step and the cleaning step; FIG. 11 is a plan view showing the relationship between the preliminary inspection sample and a cutting device according to the embodiment of the present invention; FIG. 12 is a front view showing the relationship between the preliminary inspection sample and the cutting device according to the embodiment of the present invention; FIG. 13 is a first front view showing a second cutting step according to the embodiment of the present invention; FIG. 14 is a second front view showing the second cutting step according to the embodiment of the present invention; FIG. 15 is a perspective view showing an inspection sample associated with the embodiment of the present invention; and FIG. 16 is a front view showing a drying step according to the embodiment of the present invention.

In FIG. 3, reference numeral 10 denotes a packaging container; reference numeral 12 denotes an inspection sample; reference numeral 30 denotes an inspection sample making apparatus for making the inspection sample 12; reference numeral 31 denotes a seal condition inspection apparatus for inspecting seal portions of the inspection sample 12 for seal condition; reference numeral 51 denotes a conveyor, which serves as a conveying device; and reference numeral 52 denotes a preliminary inspection sample.

Reference numeral p1 denotes a first accumulation section, and reference numeral p2 denotes a second accumulation section. The conveyor 51 is disposed between the first and second accumulation sections p1 and p2. First to fourth stop positions Sp1 to Sp4 are set along the conveyor 51. When an object of conveyance, such as the packaging container 10, the preliminary inspection sample 52, or the inspection sample 12, conveyed on the conveyor 51 reaches a predetermined stop position, the conveyor 51 is caused to halt for a predetermined time. Thus, the conveyor 51 is caused to run intermittently through activation of an unillustrated conveyor motor, such as a servomotor, which serves as a conveyor drive section.

A first work station Sn1 for carrying out a preliminary-inspection-sample-making step, a second work station Sn2 for carrying out a first cutting step and a cleaning step, a third work station Sn3 for carrying out a second cutting step, and a fourth work station Sn4 for carrying out a drying step are disposed on one side—in the present embodiment on the left-hand side—with respect to the running direction of the conveyor 51, in correspondence with the first to fourth stop positions Sp1 to Sp4, respectively.

Unillustrated first and second moving mechanisms are disposed at the first to fourth stop positions Sp1 to Sp4 in order to move objects of conveyance between the first to fourth stop positions Sp1 to Sp4 and the first to fourth work stations Sn1 to Sn4, respectively. Notably, in the present embodiment, the first moving mechanism is adapted to simultaneously move objects of conveyance between the first and second stop positions Sp1 and Sp2 and the first and second work stations Sn1 and Sn2, respectively; and the second moving mechanism is adapted to simultaneously move objects of conveyance between the third and fourth stop positions Sp3 and Sp4 and the third and fourth work stations Sn3 and Sn4, respectively.

The first and second moving mechanisms include traversers supported in such a manner as to be movable between the first to fourth stop positions Sp1 to Sp4 and the first to fourth work stations Sn1 to Sn4, respectively; chains for moving the corresponding traversers; two vacuum pads disposed at the distal end of each of the traversers and serving as a first holding-power-generating member; and a vacuum pump or the like serving as a vacuum source for generating a negative pressure within the vacuum pads. The traversers vacuum-chuck corresponding objects of conveyance through generation of a vacuum pressure within the vacuum pads, and move the objects of conveyance between the first to fourth stop positions Sp1 to Sp4 and the first to fourth work stations Sn1 to Sn4, respectively.

In the thus-configured inspection sample making apparatus 30, some packaging containers 10 are selected for inspection purpose from among the packaging containers 10 ejected from the filling apparatus in accordance with a predetermined rule and are accumulated in the first accumulation section p1 by means of an unillustrated chute, which serves as a predetermined accumulation device. Subsequently, a loading process means of an unillustrated control section performs a loading process to thereby activate an unillustrated pusher device. The pusher device pushes out the bottom packaging container 10 from the chute, thereby placing the packaging container 10 onto the conveyor 51. Next, a conveying process means of the control section performs a conveying process to thereby activate the conveyor motor. Thus, the conveyor 51 is caused to run, thereby conveying the packaging container 10.

When the packaging container 10 reaches the first stop position Sp1, the conveying process means causes the conveyor motor to stop, thereby stopping the conveyor 51. Subsequently, a moving process means of the control section performs a moving process to thereby activate the first moving mechanism. The first moving mechanism moves the packaging container 10 from the first stop position Sp1 to the first work station Sn1. In the first work station Sn1, the preliminary-inspection-sample-making step is carried out, whereby the packaging container 10 is formed into a preliminary inspection sample 52, which serves as a primary, preliminary inspection sample.

Thus, a preliminary-inspection-sample-making device 20 as shown in FIGS. 4 and 5 is disposed in the first work station Sn1. The preliminary-inspection-sample-making device 20 includes first and second unfolding devices 55 and 56 for peeling the top flaps 10g and 10h, which serve as a first fusion-bonded piece or a first lug, off the side walls 10c and 10d, respectively, of the packaging container 10; third and fourth unfolding devices 57 and 58 for peeling bottom flaps 10i and 10j, which serve as a second fusion-bonded piece or a second lug, off the bottom wall 10f of the packaging container 10; an unillustrated first positioning mechanism for vertically and horizontally moving the first and second unfolding devices 55 and 56 so as to position the first and second unfolding devices 55 and 56; and an unillustrated second positioning mechanism for vertically moving the third and fourth unfolding devices 57 and 58 so as to position the third and fourth unfolding devices 57 and 58.

Each of the first and second unfolding devices 55 and 56 includes a motor 61, such as a servomotor, which serves as an unfolding drive section; a rod 62, which is connected to the output shaft of the motor 61 and serves as an output member; and a peeling piece 63, which is connected to the distal end of the rod 62 and is formed of a thin plate shaped like a lying squarish letter U. An insert portion 65 is formed at the distal end (the lower end in FIG. 4) of the peeling piece 63. Each of the third and fourth unfolding devices 57 and 58 includes the motor 61, such as a servomotor, which serves as an unfolding drive section; the rod 62, which is connected to the output shaft of the motor 61 and serves as an output member; and a peeling piece 64, which is connected to the distal end (the upper end in FIG. 5) of the rod 62 and is formed of a thin plate shaped like a letter L. An insert portion 65 is formed at the distal end of the peeling piece 64.

The thus-configured preliminary-inspection-sample-making device 20 functions as follows. An unfolding process means of the control section performs an unfolding process to thereby activate the first positioning mechanism. The first and second unfolding devices 55 and 56 are caused to lower in the direction of arrow A and then to move in the direction of arrow B, whereby the insert portions 65 are inserted between the top flap 10g and the side wall 10c and between the top flap 10h and the side wall 10d, respectively. Subsequently, the unfolding process means activates the motors 61, thereby rotating the peeling pieces 63 180° in the direction of arrow C. As a result, the top flaps 10g and 10h are caused to rotate 180° in the direction of arrow D, to thereby be peeled off the side walls 10c and 10d, respectively.

Also, the unfolding process means activates the second positioning mechanism synchronously with the operation of the first and second unfolding devices 55 and 56, whereby the third and fourth unfolding devices 57 and 58 are caused to rise in the direction of arrow E, to thereby insert the insert portions 65 between the bottom wall 10f and the bottom flaps 10i and 10j, respectively. Subsequently, the unfolding process means activates the motors 61, thereby rotating the peeling pieces 64 180° in the direction of arrow F. As a result, the bottom flaps 10i and 10j are caused to rotate 180° in the direction of arrow G, to thereby be peeled off the bottom wall 10f.

Thus, in the first work station Sn1, the packaging container 10 undergoes the above processes and is thus formed into the preliminary inspection sample 52 as shown in FIG. 6. When the motors 61 are activated, load current flowing through the coils of the motors 61 is detected. On the basis of the detected load current, a rotation torque of each of the peeling pieces 63 and 64 is calculated.

Subsequently, the moving process means activates the first moving mechanism, thereby moving the preliminary inspection sample 52 from the first work station Sn1 to the first stop position Sp1. Then, the conveying process means again activates the conveyor motor, thereby causing the conveyor 51 to resume running for conveying the preliminary inspection sample 52.

When the preliminary inspection sample 52 reaches the second stop position Sp2, the conveying process means causes the conveyor motor to stop, thereby stopping the conveyor 51. Subsequently, the moving process means activates the first moving mechanism to thereby move the preliminary inspection sample 52 from the second stop position Sp2 to the second work station Sn2.

In the second work station Sn2, the first cutting step and the cleaning step are carried out, whereby the preliminary inspection sample 52 is cut and cleaned. Thus, as shown in FIGS. 7 to 9, the second work station Sn2 is equipped with a support table 80 for supporting the preliminary inspection sample 52. First and second holders 71 and 72, which each have a shape of a letter L, are disposed on the support table 80 for the purpose of holding the preliminary inspection sample 52. The first and second holders 71 and 72 are each supported in such a manner as to be pivotable on a predetermined point. Each of the first and second holders 71 and 72 includes a press portion 73 adapted to press a predetermined wall—in the present embodiment the front wall 10a—of the preliminary inspection sample 52; and a support portion 74 extending perpendicularly to the press portion 73. The first and second holders 71 and 72 are pivotally moved between a working position shown in FIGS. 7 and 8 and a retreat position shown in FIG. 9. The first and second holders 71 and 72 press the preliminary inspection sample 52 at the working position and release the preliminary inspection sample 52 at the retreat position.

The first and second holders 71 and 72 each have a slit 75 formed therein in such a manner as to extend along the entire length of the press portion 73 and to extend from the upper end of the support portion 74 to a predetermined position—in the present embodiment an intermediate portion—of the support portion 74.

The second work station Sn2 is further equipped with a cutting-cleaning device 70. The cutting-cleaning device 70 includes a first cutting device 90 for cutting open, at a predetermined position, the preliminary inspection sample 52 held by the first and second holders 71 and 72; and a cleaning device 67 for cleaning the preliminary inspection sample 52 that is cut open.

The first cutting device 90 includes a cutter 87, which serves as a cutting tool; a support member 68 for supporting the cutter 87; and a cutting air cylinder 69, which is attached to the support member 68 for reciprocatively moving the cutter 87 in the direction of arrow I and serves as a cutting drive section. The cutting air cylinder 69 includes a cylinder body 77; a piston 78, which is disposed within the cylinder body 77 in such a manner as to be slidable in the direction of arrow H; and a piston rod 79, which extends frontward (leftward in FIGS. 7 to 9) from the piston 78 and whose front end (left end in FIGS. 7 to 9) is connected to the support member 68. When the cutting air cylinder 69 is activated to thereby move the cutter 87 forward (leftward in FIGS. 7 to 9), the cutter 87 moves along the slit 75, thereby cutting a predetermined wall—in the present embodiment the front wall 10a, a portion of the side wall 10c, and a portion of the side wall 10d—of the preliminary inspection sample 52 along a first cutting line L1, which is set beforehand on the preliminary inspection sample 52 in the lateral direction.

The cleaning device 67 includes a pressure plate 81, which covers the substantially entire preliminary inspection sample 52 and is adapted to press the cut preliminary inspection sample 52 flat to thereby eject a liquid food from the interior of the preliminary inspection sample 52, thus serving as a press member; nozzles 82, which are attached to the pressure plate 81 at predetermined positions—in the present embodiment at positions facing the side walls 10c and 10d of the preliminary inspection sample 52—and are adapted to spray a cleaning liquid, such as water, toward the preliminary inspection sample 52 and which serve as a cleaning liquid supply section; and a cleaning air cylinder 83, which is attached to the pressure plate 81 in order to reciprocatively move the pressure plate 81 in the direction of arrow J and serves as a cleaning drive section. The cleaning air cylinder 83 includes a cylinder body 84; a piston 85, which is disposed slidably within the cylinder body 84; and a piston rod 86, which extends frontward (downward in FIG. 9) from the piston 85 and whose front end (lower end in FIG. 9) is connected to the pressure plate 81. When the cleaning air cylinder 83 is activated to thereby move the pressure plate 81 forward (downward in FIG. 9), the pressure plate 81 presses the preliminary inspection sample 52 via a predetermined wall—in the present embodiment the front wall 10a—of the preliminary inspection sample 52.

The thus-configured cutting-cleaning device 70 functions as follows. When the preliminary inspection sample 52 is moved from the second stop position Sp2 to the second work station Sn2 and is then placed on the support table 80, a first cutting process means of the control section performs a first cutting process. The first and second holders 71 and 72 are brought to the working position. The cutting air cylinder 69 is activated so as to move the cutter 87 forward, whereby the preliminary inspection sample 52 is cut along the first cutting line L1. Subsequently, the cutting air cylinder 69 is activated so as to retreat the cutter 87 (so as to move the cutter 87 rightward in FIGS. 7 to 9). Then, a cleaning process means of the control section performs a cleaning process. The first and second holders 71 and 72 are brought to the retreat position. The cleaning air cylinder 83 is activated so as to move the pressure plate 81 forward, thereby pressing the preliminary inspection sample 52 flat and ejecting a liquid food. A cleaning liquid is sprayed from the nozzles 82, thereby cleaning the preliminary inspection sample 52 in such a manner as to remove the liquid food from the inner and outer surfaces of the preliminary inspection sample 52.

In the second work station Sn2, the preliminary inspection sample 52 undergoes the above processes and is thus formed into a secondary preliminary inspection sample, which is the flat preliminary inspection sample 52 having a cut 88 as shown in FIG. 10. Notably, in FIG. 10, reference numerals L2 and L3 are second and third cutting lines that are set beforehand on the preliminary inspection sample 52 in the longitudinal direction for the purpose of cutting the preliminary inspection sample 52 in the second cutting step, which will be described later.

Subsequently, the moving process means activates the first moving mechanism to thereby move the preliminary inspection sample 52 from the second work station Sn2 to the second stop position Sp2.

As mentioned previously, at the timing of the preliminary inspection sample 52 on the conveyor 51 reaching the second stop position Sp2, the next packaging container 10 on the conveyor 51 reaches the first stop position Sp1, which is located upstream of the second stop position Sp2. When the first moving mechanism is activated to thereby move the preliminary inspection sample 52 from the second stop position Sp2 to the second work station Sn2, the packaging container 10 is moved from the first stop position Sp1 to the first work station Sn1. When, subsequently to completion of the first cutting step and the cleaning step in the second work station Sn2, the first moving mechanism is activated to thereby move the preliminary inspection sample 52 from the second work station Sn2 to the second stop position Sp2, the preliminary-inspection-sample-making step is completed, and the preliminary inspection sample 52 is moved from the first work station Sn1 to the first stop position Sp1.

Subsequently, the conveying process means again activates the conveyor motor, thereby causing the conveyor 51 to resume running for conveying the preliminary inspection sample 52.

When the preliminary inspection sample 52 reaches the third stop position Sp3, the conveying process means causes the conveyor motor to stop, thereby stopping the conveyor 51. Subsequently, the moving process means activates the second moving mechanism to thereby move the preliminary inspection sample 52 from the third stop position Sp3 to the third work station Sn3. In the third work station Sn3, the second cutting step is carried out, whereby the preliminary inspection sample 52 is cut into the inspection sample 12. For carrying out the second cutting step, as shown in FIGS. 11 and 12, a second cutting device 91 is disposed in the third work station Sn3. The second cutting device 91 cuts the preliminary inspection sample 52 into a predetermined shape. The second cutting device 91 includes lower blades 92 and 93, which are disposed in parallel with each other with a predetermined distance maintained therebetween and support the preliminary inspection sample 52 and which serves as a pair of first blades; fixing blocks 94 and 95, which are disposed above the lower blades 92 and 93 in parallel with each other with a predetermined distance maintained therebetween and in a reciprocatively movable manner and which serve as a preliminary-inspection-sample-fixing member; upper blades 96 and 97, which are disposed outside the fixing blocks 94 and 95, respectively, in parallel with each other with a predetermined distance maintained therebetween and in a reciprocatively movable manner (in a vertically movable manner in FIG. 12) and which serve as a pair of second blades; and an unillustrated cutting air cylinder, which is adapted to reciprocatively move the upper blades 96 and 97, thus serving as a cutting drive section. The fixing blocks 94 and 95 move between a frontward limit position and a backward limit position. In the frontward limit position, which serves as a fixing position, the fixing blocks 94 and 95 press the preliminary inspection sample 52 against the lower blades 92 and 93 to thereby fix the preliminary inspection sample 52. In the backward limit position, which serves as a retreat position, the fixing blocks 94 and 95 are in a retreat condition. The upper blades 96 and 97 move between a frontward limit position and a backward limit position. In the frontward limit position, which serves as a cutting position, the upper blades 96 and 97 press the preliminary inspection sample 52 against the lower blades 92 and 93 and cut the preliminary inspection sample 52. In the backward limit position, which serves as a retreat position, the upper blades 96 and 97 are in a retreat condition.

The lower blades 92 and 93 each include an elongated primary portion 101 and expanded secondary portions 102 and 103, which integrate with the primary portion 101 at corresponding opposite ends of the primary portion 101 via inclined surfaces q1 and q2, respectively. Assuming a shape corresponding to that of the lower blades 92 and 93, the upper blades 96 and 97 each include an elongated primary portion 104 and reduced secondary portions 105 and 106, which integrate with the primary portion 104 at corresponding opposite ends of the primary portion 104 via inclined surfaces q3 and q4, respectively.

When the upper blades 96 and 97 are caused to move forward (downward in FIGS. 12 to 14), a first edge e1, which is formed at the outside edge of the upper surface of each of the lower blades 92 and 93, is engaged with a second edge e2, which is formed at the inside edge of the lower surface of each of the upper blades 96 and 97 in such a manner as to correspond to the first edge e1. The preliminary inspection sample 52 is thus cut along the second and third cutting lines L2 and L3, which are set in such a manner as to correspond to the first and second edges e1 and e2.

The thus-configured second cutting device 91 functions as follows. In the initial state, the fixing blocks 94 and 95 and the upper blades 96 and 97 are brought in their retreat positions. When the preliminary inspection sample 52 is moved from the third stop position Sp3 to the third work station Sn3 and is then placed on the lower blades 92 and 93, a second cutting process means of the control section performs a second cutting process. As shown in FIG. 13, the fixing blocks 94 and 95 are caused to advance in the direction of arrow K and to be brought to the fixing position, thereby pressing the preliminary inspection sample 52 against the lower blades 92 and 93 so as to fix the preliminary inspection sample 52. Subsequently, as shown in FIG. 14, the second cutting process means causes the upper blades 96 and 97 to advance in the direction of arrow L and to be brought to the cutting position, thereby causing the first and second edges e1 and e2 to engage with each other. As a result, the preliminary inspection sample 52 is cut along the second and third cutting lines L2 and L3, whereby the inspection sample 12 is made. Notably, reference numerals 108 and 109 denote cut pieces formed in association with cutting of the preliminary inspection sample 52.

In the third work station Sn3, the preliminary inspection sample 52 undergoes the above processes and is thus formed into the inspection sample 12 as shown in FIG. 15.

The inspection sample 12 includes at least two plate-like portions. The plate-like portions are fusion-bonded together at at least a single fusion bond portion. In the present embodiment, the inspection sample 12 includes a first plate-like portion 13, which includes the back wall 10b (FIG. 2), a portion of the top wall 10e, and a portion of the bottom wall 10f; a second plate-like portion 14, which includes a portion of the front wall 10a and a portion of the top wall 10e; a third plate-like portion 15, which includes a portion of the front wall 10a and a portion of the bottom wall 10f; a first fusion bond portion 16, which includes a portion of the lateral seal portion S2 and fusion-bonds the first and second plate-like portions 13 and 14 together; and a second fusion bond portion 17, which includes a portion of the lateral seal portion S2 and fusion-bonds the first and third plate-like portions 13 and 15 together.

The first plate-like portion 13 includes a rectangular trunk portion 21, and expansion portions 22 and 23, which are formed in such a manner as to gradually expand from corresponding opposite ends of the trunk portion 21 toward the first and second fusion bond portions 16 and 17, respectively. The second plate-like portion 14 includes a trunk portion 24, and an expansion portion 25, which is formed in such a manner as to gradually expand from one end of the trunk portion 24 toward the first fusion bond portion 16. The third plate-like portion 15 includes a trunk portion 26, and an expansion portion 27, which is formed in such a manner as to gradually expand from one end of the trunk portion 26 toward the second fusion bond portion 17.

Subsequently, the moving process means activates the second moving mechanism, thereby moving the inspection sample 12 from the third work station Sn3 to the third stop position Sp3. Next, the conveying process means again activates the conveyor motor, thereby causing the conveyor 51 to resume running for conveying the inspection sample 12. When the inspection sample 12 reaches the fourth stop position Sp4, the conveying process means causes the conveyor motor to stop, thereby stopping the conveyor 51. Subsequently, the moving process means activates the second moving mechanism to thereby move the inspection sample 12 from the fourth stop position Sp4 to the fourth work station Sn4.

In the fourth work station Sn4, the drying step is carried out, whereby the inspection sample 12 is developed to an open condition and is then dried. Thus, as shown in FIG. 16, the fourth work station Sn4 is equipped with a support table 111; an opening mechanism 112 disposed on opposite sides of the support table 111; and a drying device 110, which includes a drier section 113 disposed above the inspection sample 12. The opening mechanism 112 brings the inspection sample 12 to an open condition, and the drier section 113 dries the inspection sample 12 in an open condition.

The opening mechanism 112 includes two vacuum pads 115 and 116, which are pivotably disposed on corresponding opposite sides of the support table 111 and serve as a second holding-power-generating member; and an unillustrated vacuum pump or the like serving as a vacuum source for generating a negative pressure within the vacuum pads 115 and 116. The opening mechanism 112 functions as follows. A negative pressure is generated within the vacuum pads 115 and 116 so as to vacuum-chuck the second and third plate-like portions 14 and 15. While vacuum-chucking the second and third plate-like portions 14 and 15, the vacuum pads 115 and 116 are rotated in the direction of arrow M, thereby opening the second and third plate-like portions 14 and 15; i.e., bringing the inspection sample 12 to an open condition.

The drier section 113 includes a manifold 121, which is disposed in such a manner as to extend in the longitudinal direction of the inspection sample 12; a plurality of nozzles—in the present embodiment three nozzles 122 to 124—disposed along the manifold 121; and an unillustrated hot-air-generating device, which supplies high-temperature air as drying gas, thus serving as a drying gas source. High-temperature air generated by the hot-air-generating device is supplied in the direction of arrow N; flows to the manifold 121 through a pipe line 125; and is discharged from the nozzles 122 to 124 toward the inspection sample 12. As a result, the inner surface of the inspection sample 12 is dried.

The thus-configured drying device 110 functions as follows. When the inspection sample 12 is moved from the fourth stop position Sp4 to the fourth work station Sn4 and is then placed on the support table 111, a drying process means of the control section performs a drying process. Specifically, the drying process means activates the opening mechanism 112 to thereby bring the inspection sample 12 to an open condition. Also, the drying process means activates the drier section 113 to thereby discharge high-temperature air from the nozzles 122 to 124 toward the inspection sample 12, thereby drying the inner surface of the inspection sample 12.

In the fourth work station Sn4, the inspection sample 12 undergoes the above processes and is thus developed and dried.

Subsequently, the moving process means activates the second moving mechanism, thereby moving the inspection sample 12 from the fourth work station Sn4 to the fourth stop position Sp4.

As mentioned previously, at the timing of the inspection sample 12 on the conveyor 51 reaching the fourth stop position Sp4, the next preliminary inspection sample 52 on the conveyor 51 reaches the third stop position Sp3, which is located upstream of the fourth stop position Sp4 on the conveyor 51. When the second moving mechanism is activated to thereby move the inspection sample 12 from the fourth stop position Sp4 to the fourth work station Sn4, the preliminary inspection sample 52 is moved from the third stop position Sp3 to the third work station Sn3. When, subsequently to completion of the drying step in the fourth work station Sn4, the second moving mechanism is activated to thereby move the inspection sample 12 from the fourth work station Sn4 to the fourth stop position Sp4, the second cutting step is completed, and the inspection sample 12 is moved from the third work station Sn3 to the third stop position Sp3.

Subsequently, the conveying process means again activates the conveyor motor, thereby causing the conveyor 51 to resume running for conveying the inspection sample 12 to the second accumulation section p2. In the second accumulation section p2, the sample 12 is accumulated.

The inspection samples 12 are thus made and accumulated in the second accumulation section p2. The accumulated inspection samples 12 are sent one by one to the seal condition inspection apparatus 31. The seal condition inspection apparatus 31 includes an unillustrated inspection motor, which serves as an inspection drive section; and an unillustrated rotary-body unit, which is rotated intermittently every elapse of a predetermined time through activation of the inspection motor. The rotary-body unit includes a hub connected to an output shaft of the inspection motor, and a plurality of—in the present invention six—mandrels extending radially from the hub and arranged at equal pitch spacings.

Each of the mandrels has an inspection sample holder, which is located at the distal end of the mandrel for the purpose of holding the inspection sample 12 and, thus serving as an inspection sample support portion. Each of the mandrels is caused to halt for a predetermined time at six stations ST1 to ST6 arranged in the rotational direction of the rotary-body unit.

The station ST1 is used as a loading-positioning section. The inspection sample 12 is loaded into the station ST1 at predetermined timing and is set onto the mandrel. Thus, a conveyor 131, which serves as a conveying device, is disposed in the station ST1. The sample 12 conveyed on the conveyor 131 is loaded into the station ST1.

The station ST2 is used as a first inspection section. In the station ST2, a first inspection for seal condition of a seal portion is carried out. For this inspection, an unillustrated electrostatic-capacity-type inspection equipment is disposed in opposition to the inspection sample holder. The station ST3 is used as a second inspection section. In the station ST3, a second inspection for seal condition is carried out. For this inspection, an unillustrated image-pickup-type inspection equipment is disposed in opposition to the inspection sample holder. The station ST4 serves as a spare position for adjustment of timing.

The station ST5 is used as a third inspection section. In station ST5, a third inspection for seal condition is carried out. For this inspection, a discharge-type inspection equipment is disposed in opposition to the inspection sample holder. The station ST6 is used as a delivery section for the inspection sample 12. In the station ST6, the inspection sample 12 that has been inspected for seal condition is delivered.

As described above, according to the present embodiment, in the first work station Sn1, the preliminary inspection sample 52 is made by means of the preliminary-inspection-sample-making device 20; and in the second and third work stations Sn2 and Sn3, the preliminary inspection sample 52 is cut into the inspection sample 12 by means of the first and second cutting devices 90 and 91. Thus, an operator does not need to manually make an inspection sample. Therefore, not only is work for making an inspection sample simplified, but also cutting at a wrong position is avoided. As a result, the seal condition inspection apparatus 31 can reliably inspect seal condition.

The present invention is not limited to the above-described embodiment. Numerous modifications and variations of the present invention are possible in light of the spirit of the present invention, and they are not excluded from the scope of the present invention.

INDUSTRIAL APPLICABILITY

The present invention can be applied to an inspection sample making apparatus for inspecting packaging containers for seal condition.

The invention claimed is:

1. An inspection sample making apparatus comprising:
   (a) preliminary-inspection-sample-making means, including a peeling instrument, for peeling a fusion-bonded portion of a packaging container off a wall of the packaging container so as to make a preliminary inspection sample; and
   (b) cutting means for cutting the preliminary inspection sample along a predetermined cutting line so as to make an inspection sample.

2. An inspection sample making apparatus according to claim 1, wherein the peeling instrument comprises an insert portion for insertion between the fusion-bonded portion and the wall.

3. An inspection sample making apparatus according to claim 2, wherein the peeling instrument is a thin plate.

4. An inspection sample making apparatus according to claim 1, wherein the cutting means comprises a first cutting device for cutting the preliminary inspection sample along a lateral first cutting line, and a second cutting device for cutting the preliminary inspection sample along longitudinal second and third cutting lines.

5. An inspection sample making apparatus according to claim 4, wherein the second cutting device comprises first and second blades.

6. An inspection sample making apparatus according to claim 4, wherein the first and second blades are lower blades which are parallel and are spaced apart to support the preliminary inspection sample along the second and third cutting lines, and further comprising third and fourth blades which are reciprocably driven and are arranged in parallel above the first and second blades, respectively, for cutting the preliminary inspection sample along the second and third cutting lines in cooperation with the first and second blades.

7. An inspection sample making apparatus according to claim 4, wherein said first cutting device comprises a cutting blade and reciprocating drive means for reciprocably driving said cutting blade across the first cutting line.

8. An inspection sample making apparatus according to claim 7, wherein the reciprocating drive means comprises a cylinder and a piston slidably mounted in said cylinder.

9. An inspection sample making apparatus according to claim 1, further comprising a cleaning device for cleaning the preliminary inspection sample.

10. An inspection sample making apparatus according to claim 9, wherein the cleaning device comprises a press member for ejecting a liquid food from the inside of the preliminary inspection sample.

11. An inspection sample making apparatus according to claim 10, wherein the cleaning device further comprises liquid spray nozzles for spraying a cleaning liquid onto the preliminary inspection sample.

12. An inspection sample making apparatus according to claim 1, further comprising a drying device for drying the inspection sample.

13. An inspection sample making apparatus according to claim 12, further comprising:
   (a) an opening mechanism for opening the inspection sample, wherein (b) the drying device dries the inspection sample in an opened condition.

14. An inspection sample making apparatus according to claim 1, wherein the cutting means makes an inspection sample comprising at least two plate-like portions which are fusion-bonded together at a fusion bond portion.

15. An inspection sample making apparatus according to claim 1, wherein said preliminary-inspection-sample-making means further includes rotary drive means for rotatably driving the peeling instrument.

* * * * *